(12) United States Patent
Ren et al.

(10) Patent No.: US 9,717,405 B2
(45) Date of Patent: Aug. 1, 2017

(54) VITREORETINAL MEMBRANE CHARACTERIZATION USING OPTICAL COHERENCE TOMOGRAPHY

(71) Applicant: NOVARTIS AG, Basel (CH)

(72) Inventors: Hugang Ren, Cypress, CA (US); Lingfeng Yu, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/858,541

(22) Filed: Sep. 18, 2015

(65) Prior Publication Data

US 2017/0079521 A1 Mar. 23, 2017

(51) Int. Cl.
*A61B 3/00* (2006.01)
*A61B 3/10* (2006.01)
*A61B 3/13* (2006.01)

(52) U.S. Cl.
CPC ............ *A61B 3/0025* (2013.01); *A61B 3/102* (2013.01); *A61B 3/13* (2013.01)

(58) Field of Classification Search
USPC ................................................ 351/200–246
See application file for complete search history.

(56) References Cited

U.S. PATENT DOCUMENTS

| 5,909,380 | A | * | 6/1999 | Dubois | G09B 23/28 351/205 |
| 6,186,628 | B1 | | 2/2001 | Van de Velde | |
| 8,764,189 | B2 | * | 7/2014 | Stetson | A61B 5/0059 351/205 |
| 2007/0216909 | A1 | | 9/2007 | Everett et al. | |
| 2008/0015553 | A1 | | 1/2008 | Zacharias | |
| 2013/0116670 | A1 | | 5/2013 | Artsyukhovich et al. | |

FOREIGN PATENT DOCUMENTS

| WO | 2010/117386 | 10/2010 |
| WO | 2014/106536 | 7/2014 |

OTHER PUBLICATIONS

Falkner-Radler et al., "Spectral-Domain Optical Coherence Tomography for Monitoring Epiretinal Membrane Surgery," *Ophthalmology*, vol. 117, No. 4; 8 pages, Apr. 2010.
Feron et al., "Trypan Blue Staining of Epiretinal Membranes in Proliferative Vitreoretinopathy," *Arch Ophthalmol*, vol. 120; 4 pages, Feb. 2002.
Ikagawa et al., "Chemical Toxicity of Indocyanine Green Damages Retinal Pigment Epithelium," *Physiology and Pharmacology*, vol. 46, Issue 7; 21 pages, Jul. 2005.
Koizumi et al., "Three-Dimensional Evaluation of Vitreomacular Traction and Epiretinal Membrane Using Spectral-Domain Optical Coherence Tomography," *American Journal of Ophthalmology*, vol. 145, No. 3; 10 pages, Mar. 2008.

(Continued)

*Primary Examiner* — Mohammed Hasan
(74) *Attorney, Agent, or Firm* — Baker Botts L.L.P.

(57) ABSTRACT

Optical coherence tomography (OCT) scan data is used to automatically detect and characterize vitreoretinal membranes in a spatially precise manner to generate a mask image. The mask image may characterize various aspects of a vitreoretinal membrane. The mask image is then overlaid with an optical image of the retina to enable visualization of the vitreoretinal membrane.

20 Claims, 5 Drawing Sheets

(56) References Cited

OTHER PUBLICATIONS

Ray et al., "Intraoperative Microscope-Mounted Spectral Domain Optical Coherence Tomography for Evaluation of Retinal Anatomy during Macular Surgery," *Ophthalmology*, vol. 118, No. 11; 6 pages, Nov. 2011.
Wilkins et al., "Characterization of Epiretinal Membranes Using Optical Coherence Tomography", *Ophthalmology*, vol. 103, No. 12; 10 pages, Dec. 1996.
Beutel et al., "Internal Limiting Membrane Peeling With Indocyanine Green or Trypan Blue in Macular Hole Surgery," *Arch Ophthalmol*, vol. 125; 7 pages, Mar. 2007.
International Search Report and Written Opinion of PCT Application No. PCT/IB2016/053954, mailed Sep. 26, 2016; 12 pages.
International Search Report and Written Opinion of PCT Application No. PCT/IB2016/053952, mailed Sep. 21, 2016; 10 pages.

\* cited by examiner

VITREORETINAL MEMBRANE CHARACTERIZATION USING OPTICAL COHERENCE TOMOGRAPHY

BACKGROUND

Field of the Disclosure

The present disclosure relates to ophthalmic surgery, and more specifically, to vitreoretinal membrane characterization using optical coherence tomography (OCT).

Description of the Related Art

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

In addition to viewing the fundus, some surgical microscopes may be equipped with optical scanners to provide additional information about portions of eye tissue involved with the vitreoretinal surgery. The optical scanners may be optically or electro-mechanically integrated into the surgical microscope. One type of commonly used optical scanner in ophthalmology is optical coherence tomography (OCT), which is also used during vitreoretinal surgery and may be integrated with the optics of a surgical microscope.

Furthermore, during vitreoretinal surgery, one common procedure that a surgeon may perform is peeling of membranes located on or above the vitreoretinal interface. For example, peeling of the internal limiting membrane (ILM) is performed during vitreoretinal surgery treatment of a variety of retinal conditions. Membrane peeling is a standard procedure in many vitreoretinal surgeries. However, vitreoretinal membranes, such as the ILM, are very thin and nearly transparent. Therefore, membrane peeling is a challenging task even for experienced vitreoretinal surgeons.

SUMMARY

The disclosed embodiments of the present disclosure provide a method and system to enhance vitreoretinal membrane detection, visualization, and characterization using optical scan data collected by OCT. The methods and systems disclosed herein for vitreoretinal membrane characterization using OCT may eliminate the use of membrane dyes during vitreoretinal surgery and may simplify vitreoretinal surgical procedures accordingly. The methods and systems disclosed herein for vitreoretinal membrane characterization using OCT may enable identification of the vitreoretinal interface from OCT scan data and may aid in separating membranes from the retina. The methods and systems disclosed herein for vitreoretinal membrane characterization using OCT may enhance vitreoretinal membrane detection by automatically detecting and extracting information about the membrane region from 3-dimensional (3D) OCT scan data, and subsequently overlaying the extracted membrane information onto an optical view of the fundus. The methods and systems disclosed herein for vitreoretinal membrane characterization using OCT may be used during vitreoretinal surgery and may be integrated to output an overlay image that is viewed via an oculus of a surgical microscope or an external display. The methods and systems disclosed herein for vitreoretinal membrane characterization using OCT may be used to guide a surgeon performing a membrane peeling procedure during vitreoretinal surgery. The methods and systems disclosed herein for vitreoretinal membrane characterization using OCT may be used in conjunction with diagnostic or clinical procedures that involve viewing the fundus, and in particular, the macula.

In one aspect, a disclosed method is for characterizing membranes at vitreoretinal interfaces. The method may include receiving 3D scan data of a vitreoretinal interface collected using optical coherence tomography. In the method, the 3D scan data may include line scan data for a plurality of lines. The method may include, using the line scan data corresponding to a first line included in the plurality of lines at the vitreoretinal interface, detecting the vitreoretinal interface over the first line. Based on the vitreoretinal interface detected, the method may include detecting membrane locations along the first line, the membrane locations indicative of a vitreoretinal membrane. Based on the membrane locations, the method may include generating a first line mask over the first line.

In any of the disclosed embodiments, the method may include, using a plurality of line masks, including the first line mask, corresponding to the plurality of lines, generating a mask image of the vitreoretinal interface. In the method, the mask image may describe membrane regions in 2-dimensions (2D) comprised of the membrane locations.

In any of the disclosed embodiments, the method may include, overlaying the mask image onto a corresponding optical image of the vitreoretinal interface to generate an overlay image, and outputting the overlay image to a user.

In any of the disclosed embodiments of the method, the 3D scan data and the optical image may correspond to a region-of-interest of the vitreoretinal interface selected by the user.

In any of the disclosed embodiments of the method, outputting the overlay image may further include outputting the overlay image to an oculus of a surgical microscope.

In any of the disclosed embodiments of the method, receiving the 3D scan data may further include collecting the 3D scan data using the surgical microscope.

In any of the disclosed embodiments of the method, the membrane locations may be indicative of at least one of: a detached membrane, an attached membrane, a membrane thickness, a membrane absolute position, a membrane relative position to another feature and a membrane type.

Another disclosed aspect includes an image processing system for characterizing membranes at vitreoretinal interfaces, the image processing system including a processor enable to access memory media storing instructions executable by the processor to perform the method. A further disclosed aspect includes an article of manufacture comprising non-transitory memory media for characterizing membranes at vitreoretinal interfaces, the memory media storing instructions executable by a processor to perform the method.

BRIEF DESCRIPTION OF THE DRAWINGS

For a more complete understanding of the present invention and its features and advantages, reference is now made to the following description, taken in conjunction with the accompanying drawings, in which.

Figure 1:
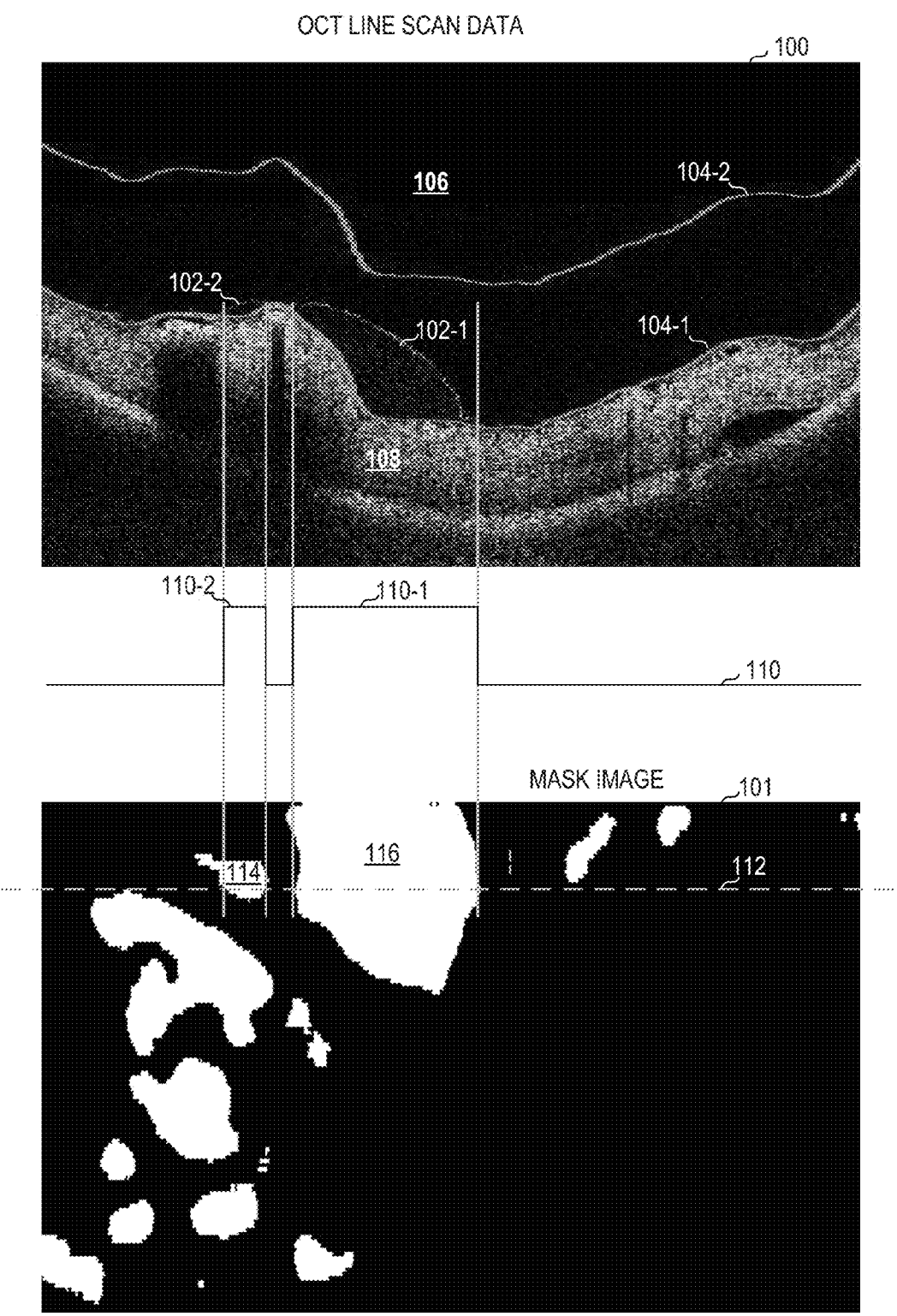
FIG. 1 shows an embodiment of OCT line scan data and a mask image.

DESCRIPTION OF PARTICULAR
EMBODIMENT(S)

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

As noted above, during vitreoretinal surgery a surgeon may view the fundus of an eye of a patient using a surgical microscope, for example, in conjunction with a contact lens placed on the cornea. In order to perform any of a variety of surgical procedures, the surgeon may peel away a membrane at the vitreoretinal interface, such as the ILM or the epiretinal membrane (ERM). Membrane peeling is a standard procedure in many vitreoretinal surgeries. For instance, ILM peeling is often performed during macular hole (MH), epiretinal membrane (ERM) as well as diabetic macular edema (DME) surgeries. However, the ILM is a thin and transparent membrane that is difficult to visualize, rendering ILM peeling a challenging task even to experienced vitreoretinal surgeons. In order to facilitate membrane peeling during vitreoretinal surgery, membrane staining with vital dyes is typically performed. The dye enhances the optical contrast of the membrane with surrounding tissues for the viewing surgeon, making membrane removal easier and less time consuming. However, dye staining of membranes, such as the ILM, involves certain procedures that may complicate or prolong vitreoretinal surgery, and may induce adverse reactions in some patients due to the toxicity of the dyes used, such as indocyanine green (ICG).

Optical coherence tomography (OCT) is a noninvasive cross-sectional imaging technique that is widely used in diagnostic and clinical ophthalmology. The capability of OCT to image vitreoretinal membranes has been demonstrated. However, direct OCT imaging may poorly display contrast between the retina and vitreoretinal membranes, limiting the visibility of the membrane. Although OCT scanners have been integrated with the optics of surgical microscopes, user operation of the resulting instrumentation may be unwieldy and impractical for use during vitreoretinal surgery. In particular, the surgeon may desire to spatially correlate the location of the optical scan, as well as scan data indicative of the profile depth scan, with the optical image from the surgical microscope, which may be difficult or time-consuming to perform during vitreoretinal surgery using different systems (i.e., the surgical microscope and the optical scanner) with independent operation and display outputs. Even when OCT scanning is integrated within a surgical microscope used for vitreoretinal surgery, interpreting a large number of unprocessed OCT images in the surgical environment to attempt to detect a precise location of a vitreoretinal membrane may be time consuming, tedious, and ineffective.

The present disclosure relates to vitreoretinal membrane detection, visualization, and characterization using image processing in place of dye staining. As will be described in further detail, OCT line scan images are used to automatically identify the vitreoretinal interface and to isolate membrane locations from the retina. A plurality of the OCT line scan images comprising 3D OCT scan data may be processed to generate a mask image showing the membrane locations. The mask image may then be overlaid with a corresponding optical image of the fundus, such as an optical image viewed by a surgeon using a surgical microscope during vitreoretinal surgery, and may assist the surgeon during a membrane peeling procedure. Other macular optical images, such as used in a diagnostic or clinical setting, may also be overlaid with the mask data to make the membrane locations visible for various purposes, such as documentation, preparation for surgery, and detection of the pathogenesis of eye disease.

Referring now to the drawings, FIG. 1 shows an embodiment of OCT line scan data 100 and a mask image 101. OCT line scan data 100 is shown as a 2D image representing a depth scan along a line at a vitreoretinal interface 104-1. The region of interest, as well as the OCT parameters, such as depth, resolution, etc., of vitreoretinal interface 104-1 may be variously selected in different embodiments of OCT line scan data 100.

In OCT line scan data 100, vitreoretinal retinal interface 104-1 may be detected using image processing as a border line between a retina 108 and the vitreous humor 106. In OCT line scan data 100, vitreoretinal interface 104-1 detected by image processing is shown as a contoured border at the edge of retina 108 and is duplicated as a second instance 104-2 to show how a region for membrane detection may be defined and limited. For example, image processing to detect membrane 102 may be limited to the image region between vitreoretinal interface 104-1 and second instance 104-2. The placement of second instance 104-2 may be performed using various methods, for example, such as a predetermined number of pixels or a given distance away from vitreoretinal interface 104-1.

In FIG. 1, against the backdrop of vitreous humor 106, a membrane 102 is visible in two sections, 102-1 and 102-2.

In some embodiments, membrane sections 102-1 and 102-2 may show detached regions of the membrane. Membrane 102 may be the ILM or another vitreoretinal membrane. Based on membrane sections 102-1 and 102-2 along vitreoretinal interface 104-1, a line mask 110 may be generated that indicates membrane locations 110-1 and 110-2. As shown, membrane locations 110-1 and 110-2 correspond spatially to membrane sections 102-1 and 102-2 respectively in length. Membrane locations 110-1 and 110-2 may be used in various embodiments to designate two different locations or a region between the locations. Line mask 110 as shown is generated using binary data and may indicate detached portions of membrane 102. In other embodiments, line mask 110 may be generated using numerical data to indicate various characteristics of membrane 102 in OCT line scan data 100, such as but not limited to a detached membrane, an attached membrane, a membrane thickness, a membrane position, and a membrane type. The membrane position may be an absolute position or a relative position, such as relative to another feature in the image, such as another eye tissue. For example in some embodiments (not shown) line mask 100 may be a numerical value that indicates a position of membrane 102, such as an absolute position or a relative position to another feature, such as relative to vitreoretinal interface 104-1.

Below in FIG. 1, mask image 101 represents a composite of a plurality of line masks 110. Line 112 indicates an actual position of line mask 110 corresponding to OCT line scan data 100. Accordingly, membrane region 116 corresponds to membrane section 102-1 and membrane location 110-1, while membrane region 114 corresponds to membrane section 102-2 and membrane location 110-2. By successively repeating acquisition of OCT line scan data 100 for a plurality of lines to generate 3D scan data, the remaining portions of mask image 101 may be generated as described above.

Figure 2:
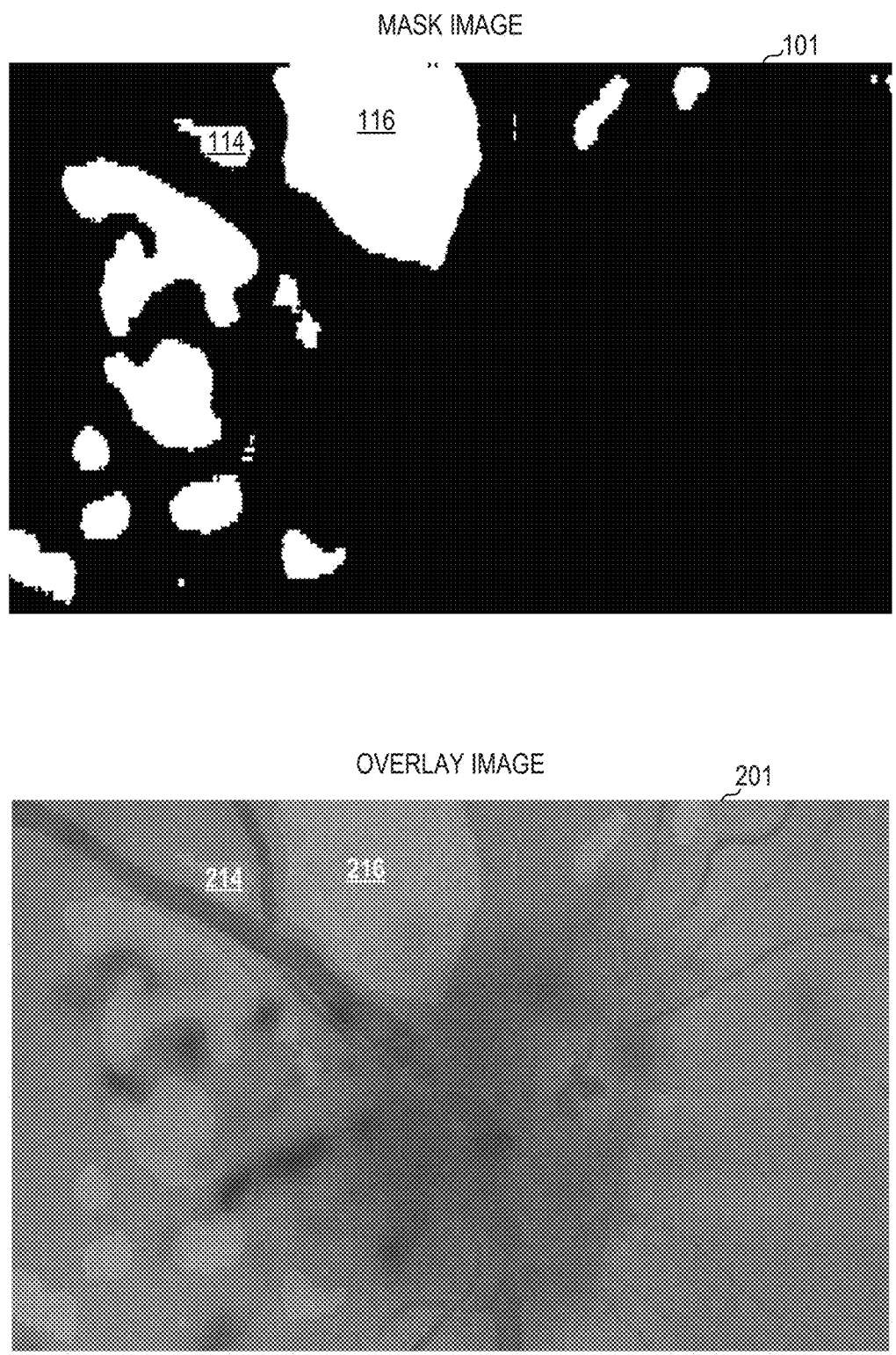
FIG. 2 shows an embodiment of a mask image and an overlay image.

FIG. 2 shows an embodiment of mask image 101 and overlay image 201. Mask image 101 includes membrane regions 114, 116, as described with respect to FIG. 1, among other membrane regions that are not labeled for descriptive clarity. Overlay image 201 is a combination of an optical image corresponding to a location of mask image 101 and mask image 101. In overlay image 201, only membrane regions of mask image 101 are shown and may be variously colored, in different embodiments. Accordingly, membrane regions 214 and 216 correspond directly to membrane regions 114 and 116, respectively.

As noted, overlay image 201 may be generated and output to an oculus of a surgical microscope that acquires the optical image. In this manner, a surgeon performing vitreoretinal surgery using the surgical microscope may be enabled to view actual membrane regions corresponding to a membrane at the vitreoretinal interface. By repeating acquisition of OCT line scan data 100 to generate successive 3D scan data, mask image 101 may be continuously updated in overlay image 201 to provide ongoing real-time contrast imaging of membrane regions. In other embodiments, overlay image 201 may be generated and output as a static image, such as for recording a state of the vitreoretinal interface of a patient for various diagnostic or clinical purposes.

Figure 3:
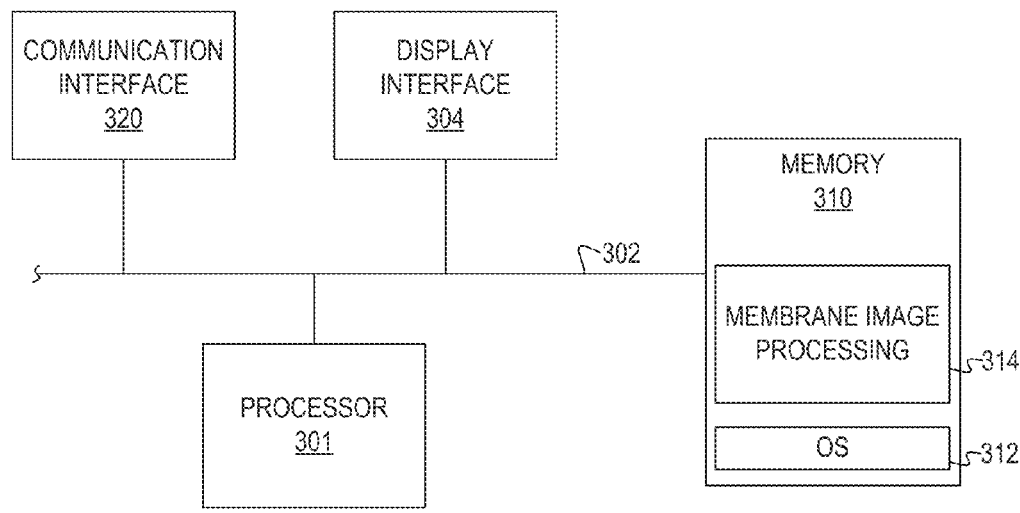
FIG. 3 is a block diagram of selected elements of an embodiment of an image processing system.

Referring now to FIG. 3, a block diagram illustrating selected elements of an embodiment of an image processing system 300 is presented. In the embodiment depicted in FIG. 3, image processing system 300 includes processor 301 coupled via shared bus 302 to memory media collectively identified as memory 310.

Image processing system 300, as depicted in FIG. 3, further includes communication interface 320 that can interface image processing system 300 to various external entities, such as an OCT scanner (not shown) to receive 2D line scan data or 3D scan data. In some embodiments, communication interface 320 is operable to enable image processing system 300 to connect to a network (not shown in FIG. 3). In embodiments suitable for control of scanning images during vitreoretinal surgery, image processing system 300, as depicted in FIG. 3, includes display interface 304 that connects shared bus 302, or another bus, with an output port for one or more displays, such as an ocular display of a surgical microscope or an display outside a surgical microscope.

In FIG. 3, memory 310 encompasses persistent and volatile media, fixed and removable media, and magnetic and semiconductor media. Memory 310 is operable to store instructions, data, or both. Memory 310 as shown includes sets or sequences of instructions, namely, an operating system 312, and a membrane image processing application 314. Operating system (OS) 312 may be a UNIX or UNIX-like operating system, a Windows® family operating system, or another suitable operating system.

In various embodiments, image processing system 300 may be integrated with different types of equipment. In one embodiment, image processing system 300 is integrated with a surgical microscope. In given embodiments, image processing system 300 may directly interface with an OCT scanner. In some embodiments, image processing system 300 is a standalone system that receives OCT scan data and optical image data, and then outputs overlay image data, as described herein.

Figure 4:
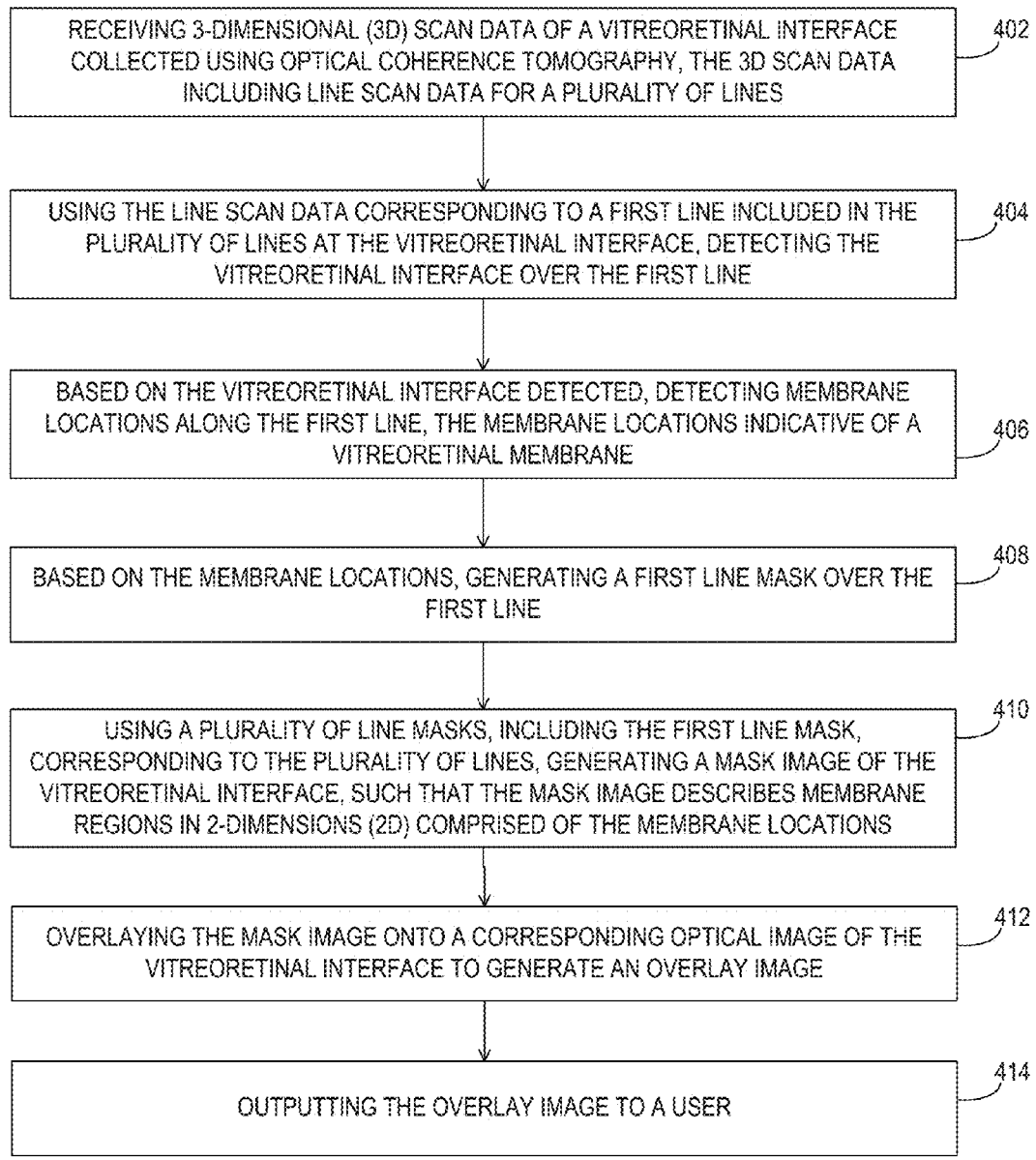
FIG. 4 is a flow chart of selected elements of a method for characterizing membranes at vitreoretinal interfaces.

Referring now to FIG. 4, a flow chart of selected elements of an embodiment of a method 400 for characterizing membranes at vitreoretinal interfaces, as described herein, is depicted in flowchart form. It is noted that certain operations described in method 400 may be optional or may be rearranged in different embodiments. Method 400 may be performed by membrane image processing application 314 in FIG. 3.

Method 400 may begin, at step 402, by receiving 3-dimensional (3D) scan data of a vitreoretinal interface collected using optical coherence tomography, the 3D scan data including line scan data for a plurality of lines. At step 404, using the line scan data corresponding to a first line included in the plurality of lines at the vitreoretinal interface, the vitreoretinal interface is detected over the first line. At step 406, based on the vitreoretinal interface detected, membrane locations along the first line are detected, the membrane locations indicative of a vitreoretinal membrane. At step 408, based on the membrane locations, a first line mask over the first line is generated. At step 410, using a plurality of line masks, including the first line mask, corresponding to the plurality of lines, a mask image of the vitreoretinal interface is generated such that the mask image describes membrane regions in 2-dimensions (2D) comprised of the membrane locations. At step 412, the mask image is overlaid onto a corresponding optical image of the vitreoretinal interface to generate an overlay image. At step 414, the overlay image is output to a user.

Figure 5:
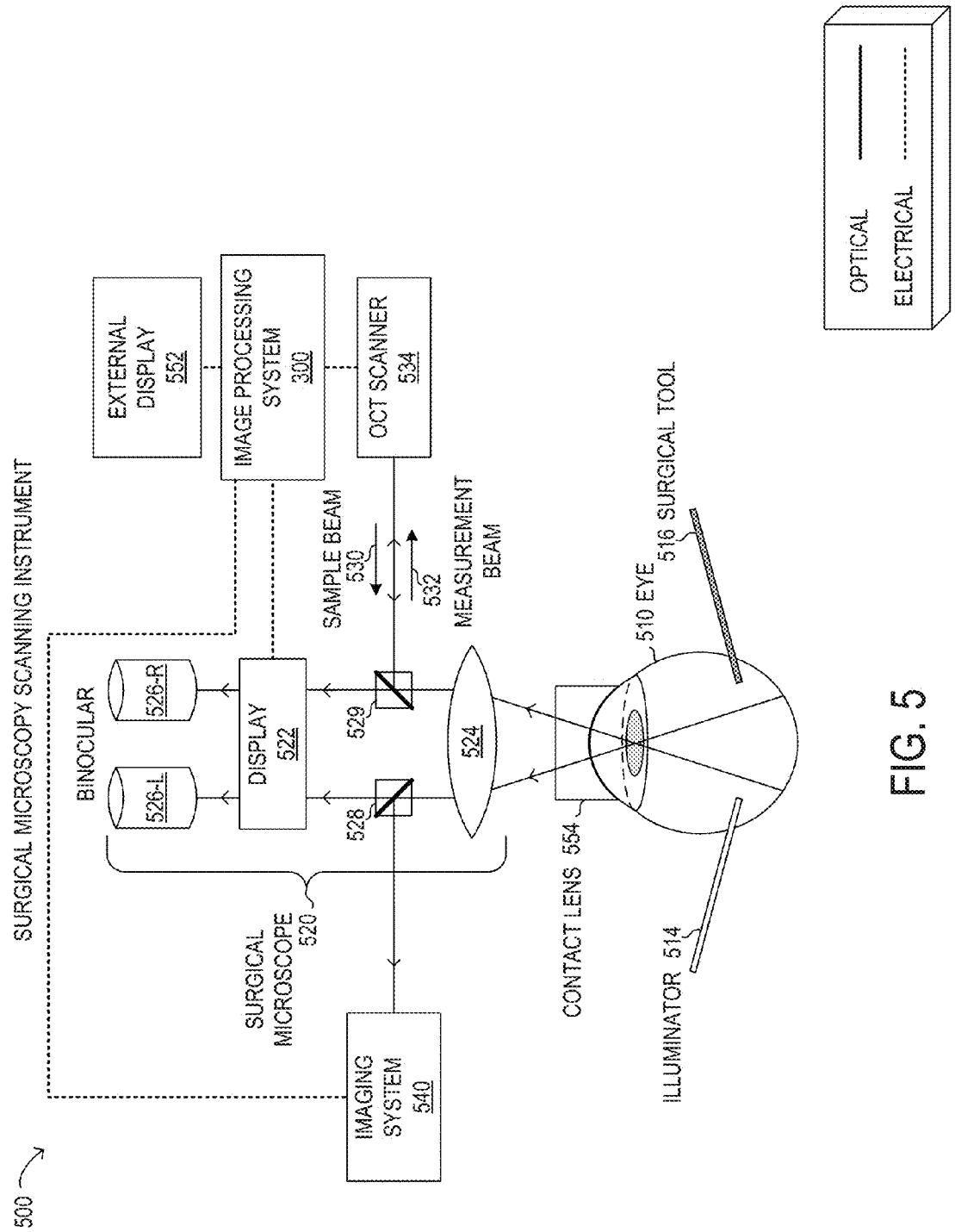
FIG. 5 is a block diagram of selected elements of an embodiment of a surgical microscopy scanning instrument.

FIG. 5 is a block diagram showing a surgical microscopy scanning instrument 500. Instrument 500 is not drawn to scale but is a schematic representation. Instrument 500 may be used during vitreoretinal surgery to view and analyze a human eye 510. As shown, instrument 500 includes surgical microscope 520, image processing system 300, external display 552, and OCT scanner 534. Also shown in FIG. 5 are imaging system 540, contact lens 554, as well as surgical tool 516 and illuminator 514.

As shown, surgical microscope 520 is depicted in schematic form to illustrate optical functionality. It will be understood that surgical microscope 520 may include various other electronic and mechanical components, in different embodiments. Accordingly, objective 524 may represent a selectable objective to provide a desired magnification or field of view of the fundus. Objective 524 may receive light from the fundus of eye 510 via contact lens 554 that rests on a cornea of eye 510. It is noted that other types of lenses at eye 510 may be used with surgical microscope 520. To perform vitreoretinal surgery, various tools and instruments may be used, including tools that penetrate the sclera, represented by surgical tool 516. Illuminator 514 may be a special tool that provides a light source from within the fundus of eye 510.

In FIG. 5, surgical microscope 520 is shown with a binocular arrangement with two distinct but substantially equal light paths that enable viewing with binoculars 526 that comprise a left oculus 526-L and a right oculus 526-R. From objective 524, a left light beam may be split at beam splitter 528, from where imaging system 540 and left oculus 526-L receive the optical image. Also from objective 524, a right light beam may be split at partial mirror 529, which also receives sample beam 530 from OCT scanner 534, and outputs measurement beam 532 to OCT scanner 534. Partial mirror 529 also directs a portion of the right light beam to right oculus 526-R. Display 522 may represent an optoelectronic component, such as an image processing system that receives data from image processing system 300 and generates overlay image 201 for left oculus 526-L and right oculus 526-R, respectively. In some embodiments, display 522 includes miniature display devices that output images to binoculars 526 for viewing by the user.

In FIG. 5, image processing system 300 may have an electrical interface with display 522, for example, for outputting display data. In this manner, image processing system 300 may receive optical image data from imaging system 540, may modify the optical image data as described herein, and may output a display image to display 522 that is viewed at binoculars 526. The display image output to display 522 or external display 552 by image processing system 300 may correspond to overlay image 201, as described previously. Because the electrical interface between display 522 and image processing system 300 may support digital image data, image processing system 300 may perform image processing in real-time with relatively high frame refresh rates. External display 552 may output similar images as display 522, but may represent a stand-alone monitor for viewing by various personnel during vitreoretinal surgery. Display 522 or external display 552 may be implemented as a liquid crystal display screen, a computer monitor, a television or the like. Display 522 or external display 552 may comply with a display standard for the corresponding type of display, such as video graphics array (VGA), extended graphics array (XGA), digital visual interface (DVI), high-definition multimedia interface (HDMI), etc.

With the binocular arrangement of surgical microscope 520 in FIG. 5, imaging system 540 may receive a portion of the left light beam that enables imaging system 540 to independently process, display, store, and otherwise manipulate light beams and image data. Accordingly, imaging system 540 may represent any of a variety of different kinds of imaging systems, as desired.

As shown, OCT scanner 534 may represent an embodiment of an optical scanner. It is noted that other types of optical scanners may be used with the arrangement depicted in FIG. 5. OCT scanner 534 may control output of sample beam 530 and may receive measurement beam 532 that is reflected back in response to photons of sample beam 530 interacting with tissue in eye 510. OCT scanner 534 may also be enabled to move sample beam 530 to the selected location indicated by the user. Image processing system 300 may interface with OCT scanner 534, for example, to send commands to OCT scanner 534 indicating the selected location to generate scan data, and to receive the scan data from OCT scanner 534. It is noted that OCT scanner 534 may represent various types of OCT instruments and configurations, as desired, such as but not limited to time domain OCT (TD-OCT) and frequency domain OCT (FD-OCT). In particular, the scan data generated by OCT scanner 534 may include two-dimensional (2D) scan data of a line scan and three-dimensional (3D) scan data for an area scan. The scan data may represent a depth profile of the scanned tissue that enables imaging below a visible surface within the fundus of eye 510, such as shown in OCT line scan data 100 (see FIG. 1).

In operation of instrument 500, the user may view the fundus of eye 510 using binoculars while vitreoretinal surgery is performed on eye 510. The user may provide user input to operate OCT scanner 534. For example, the user input may include a first indication of a selected location within the field of view for generating scan data. Image processing system 300 may then receive the scan data from OCT scanner 534 and generate mask image 101 indicative of the scan data, from which membrane locations and regions are determined, as described above. Image processing system 300 may then overlay mask image 101 on an optical image captured by surgical microscope 520, as described above. In this manner, the display image viewed by the user at binocular 526 may include the most recent updated information with regard to optical scanning.

Modifications, additions, or omissions may be made to surgical microscopy scanning instrument 500 without departing from the scope of the disclosure. The components and elements of surgical microscopy scanning instrument 500, as described herein, may be integrated or separated according to particular applications. Surgical microscopy scanning instrument 500 may be implemented using more, fewer, or different components in some embodiments.

As disclosed herein, OCT scan data is used to automatically detect and characterize vitreoretinal membranes in a spatially precise manner to generate a mask image. The mask image may characterize various aspects of a vitreoretinal membrane. The mask image is then overlaid with an optical image of the retina to enable visualization of the vitreoretinal membrane.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method for characterizing membranes at vitreoretinal interfaces, the method comprising:

receiving 3-dimensional (3D) scan data of a vitreoretinal interface collected using optical coherence tomography, wherein the 3D scan data includes line scan data for a plurality of lines;

using the line scan data corresponding to a first line included in the plurality of lines at the vitreoretinal interface, detecting the vitreoretinal interface over the first line;

based on the vitreoretinal interface detected, detecting membrane locations along the first line, the membrane locations indicative of a vitreoretinal membrane; and based on the membrane locations, generating a first line mask over the first line.

2. The method of claim 1, further comprising:

using a plurality of line masks, including the first line mask, corresponding to the plurality of lines, generating a mask image of the vitreoretinal interface, wherein the mask image describes membrane regions in 2-dimensions (2D) comprised of the membrane locations.

3. The method of claim 2, further comprising:

overlaying the mask image onto a corresponding optical image of the vitreoretinal interface to generate an overlay image; and outputting the overlay image to a user.

4. The method of claim 3, wherein the 3D scan data and the optical image correspond to a region-of-interest of the vitreoretinal interface selected by the user.

5. The method of claim 3, wherein outputting the overlay image further comprises:

outputting the overlay image to an oculus of a surgical microscope.

6. The method of claim 5, wherein receiving the 3D scan data further comprises:

collecting the 3D scan data using the surgical microscope.

7. The method of claim 1, wherein the membrane locations are indicative of at least one of: a detached membrane; an attached membrane; a membrane thickness; a membrane position; and a membrane type.

8. An image processing system for characterizing membranes at vitreoretinal interfaces, the image processing system comprising:

a processor enable to access memory media storing instructions executable by the processor to:

receive 3-dimensional (3D) scan data of a vitreoretinal interface collected using optical coherence tomography, wherein the 3D scan data includes line scan data for a plurality of lines;

using the line scan data corresponding to a first line included in the plurality of lines at the vitreoretinal interface, detect the vitreoretinal interface over the first line;

based on the vitreoretinal interface detected, detect membrane locations along the first line, the membrane locations indicative of a vitreoretinal membrane; and based on the membrane locations, generate a first line mask over the first line.

9. The image processing system of claim 8, further comprising instructions to:

using a plurality of line masks, including the first line mask, corresponding to the plurality of lines, generate a mask image of the vitreoretinal interface, wherein the mask image describes membrane regions in 2-dimensions (2D) comprised of the membrane locations.

10. The image processing system of claim 9, further comprising instructions to:

overlay the mask image onto a corresponding optical image of the vitreoretinal interface to generate an overlay image; and output the overlay image to a user.

11. The image processing system of claim 10, wherein the 3D scan data and the optical image correspond to a region-of-interest of the vitreoretinal interface selected by the user.

12. The image processing system of claim 10, wherein the instructions to output the overlay image further comprise instructions to:

output the overlay image to an oculus of a surgical microscope.

13. The image processing system of claim 12, wherein the instructions to receive the 3D scan data further comprise instructions to:

collect the 3D scan data using the surgical microscope.

14. The image processing system of claim 8, wherein the membrane locations are indicative of at least one of: a detached membrane; an attached membrane; a membrane thickness; a membrane position; and a membrane type.

15. An article of manufacture comprising non-transitory memory media for characterizing membranes at vitreoretinal interfaces, the memory media storing instructions executable by a processor to:

receive 3-dimensional (3D) scan data of a vitreoretinal interface collected using optical coherence tomography, wherein the 3D scan data includes line scan data for a plurality of lines;

using the line scan data corresponding to a first line included in the plurality of lines at the vitreoretinal interface, detect the vitreoretinal interface over the first line;

based on the vitreoretinal interface detected, detect membrane locations along the first line, the membrane locations indicative of a vitreoretinal membrane; and based on the membrane locations, generate a first line mask over the first line, wherein the membrane locations are indicative of at least one of: a detached membrane; an attached membrane; a membrane thickness; a membrane position; and a membrane type.

16. The article of manufacture of claim 15, further comprising instructions to:

using a plurality of line masks, including the first line mask, corresponding to the plurality of lines, generate a mask image of the vitreoretinal interface, wherein the mask image describes membrane regions in 2-dimensions (2D) comprised of the membrane locations.

17. The article of manufacture of claim 16, further comprising instructions to:

overlay the mask image onto a corresponding optical image of the vitreoretinal interface to generate an overlay image; and output the overlay image to a user.

18. The article of manufacture of claim 17, wherein the 3D scan data and the optical image correspond to a region-of-interest of the vitreoretinal interface selected by the user.

19. The article of manufacture of claim 17, wherein the instructions to output the overlay image further comprise instructions to:

output the overlay image to an oculus of a surgical microscope.

20. The article of manufacture of claim 19, wherein the instructions to receive the 3D scan data further comprise instructions to:

collect the 3D scan data using the surgical microscope.

* * * * *